United States Patent [19] — Ogawa et al.

[11] Patent Number: 5,047,543
[45] Date of Patent: Sep. 10, 1991

[54] 1,4-DIHYDROPYRIDINE DERIVATIVES

[75] Inventors: Toshihisa Ogawa; Tomomi Ota; Shuichi Sato, all of Ageo; Takemi Sunaga, Tokyo; Yoshiaki Watanabe, Kodaira; Katsuo Hatayama, Omiya, all of Japan

[73] Assignee: Taisho Pharmaceutical Co., Ltd., Japan

[21] Appl. No.: 437,636

[22] Filed: Nov. 17, 1989

[30] Foreign Application Priority Data

Nov. 24, 1988 [JP] Japan .................. 63-296861

[51] Int. Cl.$^5$ .......................... C07D 213/42
[52] U.S. Cl. ................................. 546/321
[58] Field of Search ............ 546/321; 514/330

[56]  References Cited

U.S. PATENT DOCUMENTS 4,472,411  9/1984  Hatayama et al. ............. 424/266
4,540,701  9/1985  Ueda .............................. 514/375
4,656,181  4/1987  Sunkel et al. ................. 514/336
4,727,066  2/1988  Sunkel et al. ................. 514/161

FOREIGN PATENT DOCUMENTS 203662  8/1988  Japan ............................. 546/321
8402132  6/1984  World Int. Prop. O. .

Primary Examiner—C. Warren Ivy
Assistant Examiner—Celia Chauj
Attorney, Agent, or Firm—Lorusso & Loud

[57] ABSTRACT

A 1,4-dihydropyridine derivative represented by the formula

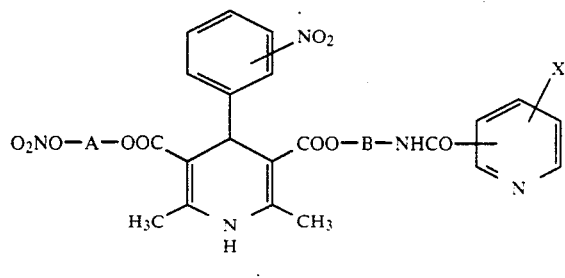

wherein X is a hydrogen atom or an alkoxy group having 1 to 4 carbon atoms, A and B are the same or different and are each an alkylene group having 1 to 4 carbon atoms, and a pharmaceutically acceptable salt thereof are useful as the preventive and therapeutical agents of ischemic heart disease and hypertension.

1 Claim, No Drawings

1,4-DIHYDROPYRIDINE DERIVATIVES

BACKGROUND OF THE INVENTION

1. Field of the Invention

The present invention relates to 1,4-dihydropyridine derivatives useful as the preventive and therapeutical agents of ischemic heart disease and hypertension.

2. Description of the Prior Art

There are the prior art 1,4-dihydropyridine derivatives described in Japanese Patent Publication No. 63-5024 and Japanese Patent Kokai No. 60-500255, nifedipine and the like. These compounds have coronary vasodilating activity due to calcium antagonism, and used as the preventive and therapeutical ischemic heart disease and hypertension. However, since these prior art 1,4-dihydropyridine derivatives have even the property to dilate the peripheral vessel due to coronary vasodilating activity, their topical activity is insufficient. Furthermore, these compounds have a drawback of poor duration of action. The compounds described in Japanese Patent Kokai No. 60-500255, while fairly improved in this action, show no increase in action of cyclic GMP (hereinafter referred to as "c-GMP"), and therefore these compounds are insufficiently effective as preventive or therapeutical agents for treatment of hypertension when compared with nitrates such as nitroglycerin. The present inventors have found novel compounds having the selective coronary vasodilating activity and increased activity of c-GMP.

SUMMARY OF THE INVENTION

An object of the present invention is to provide a 1,4-dihydropyridine derivative represented by the formula;

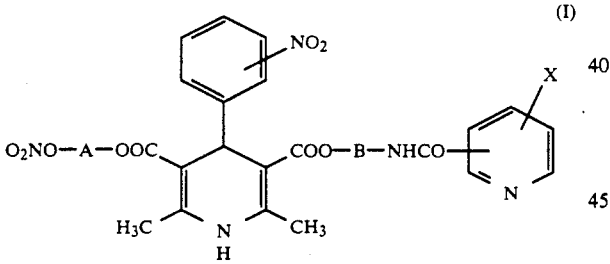

wherein X is a hydrogen atom or an alkoxy group having 1 to 4 carbon atoms, A and B are the same or different and are each an alkylene group having 1 to 4 carbon atoms, and a pharmaceutically acceptable salt thereof.

DETAILED DESCRIPTION OF THE INVENTION

In Formula (I), the alkylene group having 1 to 4 carbon atoms for A and B refers to a straight or branched chain alkylene group such as, for example, a methylene group, an ethylene group, a trimethylene group, a 1-methylethylene group, a 2-methylethylene group and a tetramethylene group.

The alkoxy group having 1 to 4 carbon atom may be a methoxy group, an ethoxy group, a propoxy group, a butoxy group and the like.

The pharmaceutically acceptable salt refers to the acid addition salts of the compound of Formula (I). Examples of the acid are inorganic acids (e.g., hydrochloric acid, hydrobromic acid, hydroiodic acid, sulforic acid and phosphoric acid) and organic acids (e.g., methanesulfonic acid, succinic acid and maleic acid).

The amide group in Formula (I) is in the 2-, 3- or 4-position of the pyridine ring.

The nitrophenyl group attached to the dihydropyridine skeleton at the 4-position is ortho or meta to the phenyl group.

Among the preferred compounds of the present invention are 2,6-dimethyl-4 (3-nitrophenyl)-1,4-dihydropyridine-3,5-dicarboxylic acid 3-(3-nitrooxypropyl) ester 5-(2-picolinoylaminoethyl) ester, 2,6-dimethyl-4-(3-nitrophenyl)-1,4-dihydropyridine-3,5-dicarboxylic acid 3-(2-nicotinoylaminoethyl) ester 5-(3-nitrooxypropyl) ester, 2,6-dimethyl-4-(3-nitrophenyl)-1,4-dihydropyridine-3,5-dicarboxylic acid 3-(2-nicotinoylaminoethyl) ester 5-(3-nitrooxypropyl) ester hydrochloride and 2,6-dimethyl-4-(3-nitrophenyl)-1,4-dihydropyridine-3,5-dicarboxylic acid 3-(3-nicotinoylaminopropyl) ester 5-(3-nitrooxypropyl) ester.

The 1,4-dihydropyridine derivatives of the present invention can be prepared, for example, according to the following processes.

Process (1): A benzaldehyde derivative of the formula;

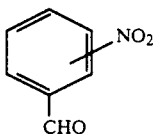

(wherein X is as defined above), an acetoacetate of the formula

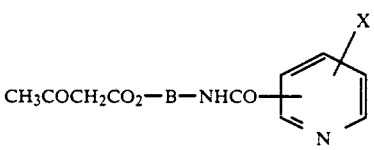

(wherein B and X are as defined above) and 3-aminocrotonate of the formula

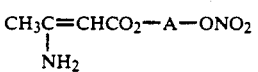

(wherein A is as defined above) are together heated in an organic solvent or without solvent to give a compound of the present invention. The organic solvents used in the reaction may be methanol, ethanol, 2-propanol, dioxane, tetrahydrofuran, benzene and toluene. The reaction conditions can be varied appropriately.

Process (2): The compound of Formula (II) is reacted with the compound of Formula (III in the presence of a secondary amine or an organic or inorganic acid salt thereof in an organic solvent at 0° to 150° C. to give a benzilidene derivative of the formula

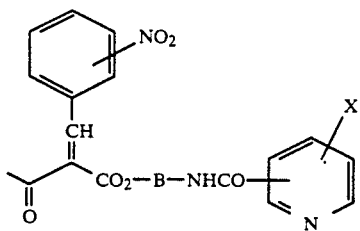

(wherein B and X are as defined above), which is then reacted with a compound of Formula (IV) in an organic solvent or without solvent with heating at 50 to 100° C. to give the compound of the present invention.

Examples of the secondary amine are dimethylamine, diethylamine, diisopropylamine, pyrolidine, piperidine, piperazine, N-methylpiperazine and morpholine Examples of the inorganic acid salt of the secondary amine are salts with hydrochloric acid, sulfonic acid, nitric acid, hydrobromic acid and phosphoric acid Examples of the organic acid salt of the secondary amine are salts with formic acid, acetic acid, trifluoroacetic acid, propionic acid, benzoic acid and p-toluenesulfonic acid The organic solvents used may be methanol, ethanol, 2-propanol, dioxane, tetrahydrofuran, benzene and toluene.

Process (3): A compound of the formula

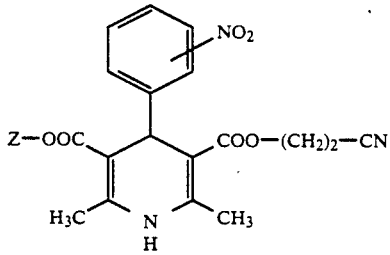

[wherein Z is a group of the formula

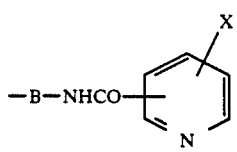

(wherein B and X are as defined above) or a group of the formula

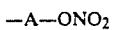 (VI)

(wherein A is as defined above)], obtained by a process similar to Process (1) or (2), is hydrolyzed to give a carbonic acid of the formula

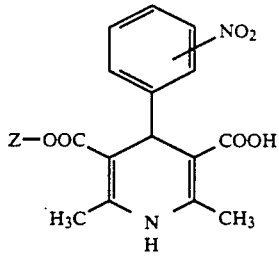

(wherein Z is as defined above). Then, either a reaction of the compound of Formula (VII) wherein Z is a group of Formula V with a compound of the formula HO—A—ONO$_2$ (wherein A is as defined above) or a reaction of the compound of Formula (VII) wherein Z is a group of Formula (VI) with a compound of the formula

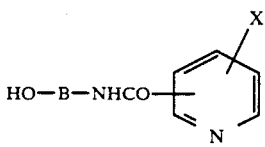

(wherein B and X are as defined above) gives the compound of Formula (I).

The starting materials of the present invention can be prepared as follows;

The compound of Formula (VIII) can be prepared by reacting a compound of the formula

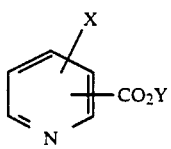

(wherein X is as defined above, and Y is a residue of any alcohol) with a compound of the formula H$_2$N—B—OH (wherein B is as defined above) under the conditions described in Pharmacological Bulletin, vol 80, page 1706 (1960).

The compound of Formula (III) can be prepared by reacting the compound of Formula (V) with diketene under the conditions described in J. Chem. Soc., vol 97, page 1978 (1910)

The compounds of Formula (I) of the present invention have the remarkable properties in the selective coronary vasodilating activity, the duration action and the increase effect of c-GMP, and therefore these compounds are useful as the preventive and therapeutical agents of ischemic heart disease and hypertension. For the purpose, these compounds can be administered orally or parenterally in a conventional dosage forms such as tablets, powders, granules, capsules, solutions and injectional solutions, each of which can be prepared in accordance with ordinary pharmaceutical practices.

The dose of these compounds depends on the age, body weight, response of the patients, route of the administration or time of the administration, but usually it may be from 1 to 200 mg/day.

The present invention is illustrated by the following examples in more detail

EXAMPLE 1

2,6-Dimethyl-4-(3-nitrophenyl)-1,4-dihydropyridine-3,5-dicarboxylic acid 3-(3-nitrooxypropyl) ester 5-(2-picolinoylaminoethyl) ester (Compound 1)

A solution of 9.07 g (0.06 mole) of m-nitrobenzaldehyde, 15.00 g (0.06 mole) of 2-picolinoylaminoethyl acetoacetate, 12.24 g (0.06 mole) of 3-nitrooxypropyl 3-aminocrotonate and 1.74 g (0.012 mole) of piperidinium acetate in 200 ml of 2-propanol was refluxed for 4 hours. After the reaction, the solvent was evaporated, and the residue was purified by silica gel column chromatography [eluent; ethyl acetate hexane (1:3)] to give 20.45 g of the title compound.

m.p. 146°–148° C.

$^1$H-NMR (CDCl$_3$) δ ppm: 2.02 (2H, quintet, J=6Hz), 2.38 (6H, s), 3.6–3.9 (2H, m), 4.0–4.4 (6H, m), 5.08 (1H, s), 5.81 (1H, s), 7.30 (1H, t, J=8Hz), 7.44 (1H, dd, J=6Hz, 8Hz), 7.65 (1H, d, J=8Hz), 7.86 (1H, t, J=8Hz), 7.96 (1H, d, J=8Hz), 8.11 (1H, s), 8.17 (1H, d, J=8Hz), 8.0–8.2 (1H, m), 8.52 (1H, d, J=6Hz).

EXAMPLE 2

2,6-Dimethyl-4-(3-nitrophenyl)-1,4-dihydropyridine-3,5-dicarboxylic acid 3-(2-nicotinoylaminoethyl) ester 5-(3-nitrooxypropyl) ester hydrochloride (Compound 3)

A solution of 9.07 g (0.06 mole) of m-nitrobenzaldehyde, 15.0 g (0.06 mole) of 2-nicotinoylaminoethyl acetoacetate and 1.74 g (0.012 mole) of piperidinium acetate in 100 ml of benzene was heated at reflux under azeotropic dehydration conditions for 2 hours. After the reaction, the mixture was extracted with benzene, and the extract was washed with water and dried over anhydrous sodium sulfate. Evaporation of the solvent under reduced pressure gave 19.82 g of 2-nicotinoylaminoethyl 3-nitrobenzilideneacetoacetate as white crystals.

To a mixture of 3.71 g(0.01 mole) of this compound and 2.04 g (0.01 mole) of 3-nitrooxypropyl 3-aminocrotonate, was added 20 ml of 2-propanol, and the mixture was heated at reflux for 3 hours. After the reaction, the solvent was evaporated under reduced pressure, the residue was chromatographed on a silica gel column [eluent; ethyl acetate—hexane (1:1)] and then recrystallized from methanol—ether to give 2.56 g of 2,6-dimethyl-4-(3-nitrophenyl)-1,4-dihydropyridine-3,5-dicarboxylic acid 3-(2-nicotinoylaminoethyl) ester 5-(3-nitrooxypropyl) ester (Compound 2) as yellow crystals.

m.p. 101°–012° C.

$^1$H-NMR (CDCl$_3$) δ ppm: 1.92 (2H, m), 2.28 (3H, s), 2.31 (3H, s), 3.54 (2H, m), 4.01 (2H, m), 4.12 (2H, m), 4.38 (2H, t, J=7Hz), 5.00 (1H, s), 7.36–7.68 (3H, m), 7.80–8.05 (2H, m), 8.15 (1H, m), 8.71 (1H, dd, J=2Hz, 5Hz), 8.75 (1H, t, J=5Hz), 8.98 (1H, d, J=2Hz), 9.09 (1H, s).

Into a solution of Compound 2 in chloroform was introduced hydrogene chloride gas, and evaporation of the solvent under reduced pressure gave the title compound.

m.p. 106°–108° C.

Following a process similar to that of Example 2, the following compounds were synthesized.

2,6-Dimethyl-4-(3-nitrophenyl)-1,4-dihydropyridine-3,5-dicarboxylic acid 3-(3-nicotinoylaminopropyl) ester 5-(3-nitrooxypropyl) ester (Compound 4)

m.p. 135°–137° C.

$^1$H-NMR (CDCl$_3$) δ ppm: 1.83 (2H, m), 1.98 (2h, m), 2.31 (3H, s), 2.34 (3H, s), 3.31 (2H, m), 4.02 (2H, m), 4.05 (2H, m), 4.42 (2H, t, J=8Hz), 4.98 (1H, s), 7.43–7.73 (3H, m), 7.93–8.06 (2H, m), 8.15 (1H, m), 8.65 (1H, t, J=5Hz), 8.68 (1H, dd, J=5Hz, 8Hz), 8.97 (1H, d, J=2Hz), 9.09 (1H, s).

2,6-Dimethyl-4-(3-nitrophenyl)-1,4-dihydropyridine-3,5-dicarboxylic acid 3-(1-methyl-2nicotinoylaminoethyl) ester 5-(3-nitrooxypropyl) ester m.p. 127°–129° C.

$^1$H-NMR (CDCl$_3$) δ ppm: 1.20 (3H, d, J=8Hz), 1.95 (2H, m), 2.28 (3H, s), 2.30 (3H, s), 3.35 (2H, m), 4.03 (2H, m), 4.42 (2H, t, J=7Hz), 4.94 (1H, s), 4.96 (1H, m), 7.46–7.52 (2H, m), 7.57 (1H, m), 8.82–8.98 (2H, m), 8.06 (1H, m), 8.65 (1H, t, J=5Hz), 8.70 (1H, dd, J=2Hz, 5Hz), 8.88 (1H, d, J=2Hz), 9.05 (1H, s).

2,6-Dimethyl-4-(2-nitrophenyl)-1,4-dihydropyridine-3,5-dicarboxylic acid 3-(2-nicotinoylaminoethyl) ester 5-(3-nitrooxypropyl) ester (Compound 5)

m.p. 137°–138° C.

$^1$H-NMR (CDCl$_3$) δ ppm: 1.86 (2H, m), 2.22 (3H, s), 2.27 (3H, s), 3.47 (2H, m), 3.96 (2H, m), 4.15 (2H, m), 4.34 (2H, t, J=7Hz), 5.59 (1H, s), 7.23–7.70 (5H, m), 8.12 (1H, m), 8.66 (1H, t, J=5Hz), 8 71 (1H, dd, J=2Hz, 5Hz), 8.96 (1H, d, J=2Hz), 9.02 (1H, s).

2,6-Dimethyl-4-(3-nitrophenyl)-1,4-dihydropyridine-3,5-dicarboxylic acid 3-(3-isonicotinoylaminopropyl) ester 5-(3-nitrooxypropyl) ester (Compound 6)

m.p. 144°–145° C.

$^1$H-NMR (CDCl$_3$) δ ppm 1.82 (2H, m), 1 96 (2H, m), 2.28 (3H, s), 2.30 (3H, s), 3 31 (2H, m), 4.02 (2H, t, J=5Hz), 4.05 (2H, m), 4.42 (2H, t, J=7Hz), 4.98 (1H, s), 7.40–8 15 (6H, m), 8 68–8.85 (3H, m), 9.07 (1H, s).

2,6-Dimethyl-4-(3-nitrophenyl)-1,4-dihydropyridine-3,5-dicarboxylic acid, 3-(2-nicotinoylaminopropyl) ester 5-(3-nitrooxypropyl) ester (Compound 7)

m.p. 130°–133° C.

$^1$H-NMR (CDCl$_3$) δ ppm: 1.22 (3H, d, J=6Hz), 2.02 (2H, quintet, J=6Hz), 2.37 (3H, s), 2.38 (3H, s), 4.0–4.5 (7H, m), 5.08 (1H, s), 6.03 (1H, s), 6.57 (1H, each d, J=8Hz), 7.2–7.4 (2H, m), 7.58 (1H, t, J=8Hz), 7.8–8.1 (3H, m), 8.71 (1H, d, J=6Hz), 8.84 (1H, s).

2,6-Dimethyl-4-(3-nitrophenyl)-1,4-dihydropyridine-3,5-dicarboxylic acid 3-[2-(6-methoxynicotinoylamino)ethyl] ester 5-(3-nitrooxypropyl) ester $^1$H-NMR (CDCl$_3$ 200 MHz) δ ppm: 2.03 (2H, quintet, J=3Hz, 6Hz), 2.38 (3H, s), 2.39 (3H, s), 3.62–3.75 (2H, m), 4.00 (3H, s), 4.10–4.22 (2H, m), 4.28–4 40 (2H, m), 4.38 (2H, t, J=3Hz, 6Hz), 5.08 (1H, s), 6.05 (1H, s), 6.42 (1H, t, J=5Hz), 6.76 (1H, d, J=8Hz), 7.33 (1H, t, J=8Hz), 7.62 (1H, d, J=8Hz), 7.90 (1H, d, J=8Hz), 7.96 (1H, d, J=8Hz), 8.11 (1H, s), 8.42 (1H, s).

EXAMPLE 3

2,6-Dimethyl-4-(3-nirtrophenyl)-1,4-dihydropyridine-3,5-dicarboxylic acid 3-(2-nicotinoylaminoethyl) ester 5-(2-nitrooxypropyl) ester To a solution of 25.03 g (100 mole) of 2-nicotinoylaminoethyl acetoacetate, 15.11 g (100 mmole) of m-nitrobenzaldehyde and 15.42 g (100 mmole) of 2-cyanoethyl 3-aminocrotonate in 150 ml of isopropyl alcohol was added 0.73 g (5 mmole) of piperidinium acetate, and the mixture was refluxed for 5 hours. After evaporation of the solvent, the residue was dissolved in 200 ml of acetone. To the solution was added 200 ml of 0.75 N aqueous sodium hydroxide solution, and the mixture was stirred at room temperature for an hour. 1N hydrochloric acid was added, and the solution was concentrated and extracted with chloroform Evaporation of the solvent gave 45.27 g of 2,6-dimethyl4-(3-nitrophenyl)-1,4-dihydropyridine-3,5-dicarboxylic acid 3-(2-nicotinoylaminoethyl) ester.

m.p. 151.0°–152.0° C.

$^1$H-NMR (DMSO-$d_6$, 200 Mz) δ ppm 2.28 (6H, s), 3.51 (2H, q, J=6Hz), 4.13 (2H, t, J=6Hz), 4.99 (1H, s), 7.42 (1H, t, J=8Hz), 7.50 (1H, d, J=8Hz), 7.60 (1H, d, J=8Hz), 7.93 (1H, d, J=8Hz), 7.98 (1H, s), 8.13 (1H, d, J=8Hz), 8.71 (1H, d, J=5Hz), 8.57–8.78 (1H, m), 8.94 (1H, s), 8.96 (1H, s), 11.83 (1H, br, s).

To a solution of 1.87 g (4 mmole) of the compound obtained above and 32.66 g (320 mmole) of acetic anhydride in 20 ml of dichloromethane was added 2.0 g of molecular sieves 3A, and the mixture was stirred at room temperature for 15 hours. After removal of the solids, 0.58 g (4.8 mmole) of 2-nitrooxy-1-propanol was added, and the mixture was neutralized with a few drops of acetyl chloride and extracted with chloroform. The extract was washed with brine and dried over magnesium sulfate Evaporation of the solvent gave an oil, which was then purified by silica gel column chromatography [eluent; ethyl acetate—hexane (2 : 1)] and recrystallization from methanol—diethyl ether to give 1.20 g of the title compound.

$^1$H-NMR (CDCl$_3$, 200 MHz). δ ppm: 1.26, 1.32 (3H, each d, J=8Hz), 2.37 (3H, s), 2.38 (3H, s), 3.63–3.78 (2H, m), 4.04, 4.10 (1H, each t, J=7Hz), 4.21–4.28 (1H, m), 4.33 (2H, t, J=5Hz), 5.05 (1H, s), 5.31 (1H, d, quintet, J=3Hz, 7Hz), 6.22 (1H, s), 6.74 (1H, t, J=5Hz), 7.31 (1H, t, J=8Hz), 7.38 (1H, dd, J=5Hz, 8Hz), 7.59 (1H, d, J=8Hz), 7.94 (1H, d, J=8Hz), 8.04 (1H, d, J=8Hz), 8.08 (1H, s), 8.72 (1H, d, J=5Hz), 8.87 (1H, s).

Following a procedure similar to that of Example 3, there were synthesized the following compounds.

2,6-Dimethyl-4-(2-nitrophenyl)-1,4-dihydropyridine-3,5-dicarboxylic acid 3-(2-nicotinoylaminoethyl) ester 5-(2-nitrooxypropyl) ester $^1$H-NMR (CDCl$_3$) δ ppm: 1.23 (3H, d, J=7Hz), 2.36 (6H, s), 3.69 (2H, q, J=5Hz), 3.98–4.50 (4H, m), 5.14–5.34 (1H, m), 5.78 (1H, each s), 5.81 (1H, each s), 6.26 (1H, s), 7.06–7.57 (5H, m), 7.64 (1H, d, J=7Hz), 8.17 (1H, t, J=7Hz), 8.75 (1H, br.s), 9.03 (1H, br.s).

Experiment 1:

Selective coronary vasodilating activity test

Male and female mongrel dogs weighing 8 to 15 kg were anesthetized with sodium pentobarbital (30 mg/kg, i.e.), and thoracotomized under artificial respiration. The heparinized autoblood was perfused through the coronary and femoral arteries into which the cannulas were each inserted to give the extracorporeal circulatory paths. As test compounds were used Compounds 1, 3, 4, 5 and 7 of the present invention and well-known nifedipine, 2,6-dimethyl-4-(3-nitrophenyl)-1,4-dihydropyridine-3,5-dicarboxylic acid 3-methyl ester -(2-nicotinoylaminoethyl) ester (Compound A) and 2,6-dimethyl-4-(3-nitrophenyl)-1,4-dihydropyridine-3,5-dicarboxylic acid 3-(2-nitrooxypropyl) ester 5-(3-nitrooxypropyl) ester (Compound B). Each test compound dissolved in dimethyl sulfoxide was administered intraarterially, and the blood flow was measured by means of the electromagnetic blood flow meter of which the blood flow probe was inserted to the extracorporeal circulatory path. The dosages of the compounds of the present invention and the prior art compound were each chosen so as to show the same degree of the increase of the blood flow in the coronary artery each other (e.g., dosages of the compounds of the present invention and Compound A were each 30 μg, and those of nifedipine and Compound B were each 1 μg. The value of the blood flow of the femoral artery/the blood flow of the coronary artery is calculated as an indication of the selective coronary vasodilating activity, and the data are shown in Table 1 as compared to 1 of the value of nifedipine.

Experiment 2

Duration Test of the duration of the drug effect

The change of the blood flow in the coronary artery in Experiment 1 was measured, and the duration of the action is expressed as the time (minutes) up to which the maximum blood flow of the coronary artery is reduced to one-half its volume. Results are shown in Table 1.

TABLE 1

| Test Compound | Coronary-selectivity | Duration time (min.) |
| --- | --- | --- |
| Compound 1 | 1.5 | 9.2 |
| Compound 2 | 3 | |
| Compound 3 | 3 | 32.9 |
| Compound 4 | 2 | 7.1 |
| Compound 5 | 2 | 4.1 |
| Compound 7 | 2 | 4.2 |
| nifedipine | 1 | 1.0 |
| Compound A | 1.5 | 3.5 |
| Compound B | 2 | 3.0 |

EXPERIMENT 3

Increase effect of c-GMP

Male and female mongrel dogs weighing 8 to 15 kg were anesthetised with 30 mg/kg of sodium pentobarbital intravaneously. After removal of the blood, the femoral artery was dissected. The blood vessel was suspended in a vessel containing an oxygenated nutrient solution, after which the test drug was added into the vessel for the reaction. The dosages and administration routes were the same as those used in the selective coronary vessel dilation test described above.

Samples for radioimmunoassay (RIA) were prepared using the homogenized blood vessel, and c-GMP was measured using a kit to calculate the minimum effective concentration required to significantly increase c-GMP. Results are shown in Table 2.

TABLE 2

| Test Compound | Minimum effective concentration (M)* |
| --- | --- |
| Compound 3 | $10^{-6}$ |
| Compound 4 | $10^{-6}$ |
| nifedipine | — |
| Compound A | — |
| Compound B | $10^{-5}$ |

In Table 2, minus (—) means the lack of increase of c-GMP.

What is claimed is:

1. A 2,6-Dimethyl-4-(3-nitrophenyl)-1,4-dihydropyridine-3,5-dicarboxylic acid 3-(2-nicotinoylaminoethyl) ester 5-(3-nitrooxypropyl ester and pharmaceutically acceptable salts thereof.

* * * * *

UNITED STATES PATENT AND TRADEMARK OFFICE
CERTIFICATE OF CORRECTION

PATENT NO. : 5,047,543
DATED : September 10, 1991
INVENTOR(S) : OGAWA et al

It is certified that error appears in the above-identified patent and that said Letters Patent is hereby corrected as shown below:

Col. 1, line 30, after "having" delete "the"; and line 62, delete "atom" and insert --atoms--.

Col. 2, line 65, "(III" should read --(III)--.

Col. 3, line 21, after "morpholine" insert a period --.--;

line 25, after "acid" insert a period --.--; and line 30, after "acid" insert a period --.--.

Col. 4, line 51, after "(1910)" insert a period --.--.

Col. 5, line 14, "acetate hexane" should read --acetate-hexane--;

line 29, "3)", centered, should read --3)-- at the left hand margin; and line 54, "012°" should read --102°--.

Col. 6, line 42, "1 96" should read --1.96--; and line 64, "4 40" should read --4.40--.

Col. 7, line 17, after "chloroform" insert a period

UNITED STATES PATENT AND TRADEMARK OFFICE
CERTIFICATE OF CORRECTION

PATENT NO. : 5,047,543

DATED : September 10, 1991

INVENTOR(S) : OGAWA et al

Page 2 of 2

It is certified that error appears in the above-identified patent and that said Letters Patent is hereby corrected as shown below:

--.--;

line 36, after "sulfate" insert a period --.--.

Col. 8, line 6, "-(2-nicotinoylaminoethyl)" should read --5-(2-nicotinoylaminoethyl)--; and line 30, "Duration Test" should read --Test--.

Signed and Sealed this

Nineteenth Day of January, 1993

Attest:

DOUGLAS B. COMER

Attesting Officer

Acting Commissioner of Patents and Trademarks